United States Patent
Dougherty et al.

(10) Patent No.: US 6,255,538 B1
(45) Date of Patent: Jul. 3, 2001

(54) PROCESS FOR THE C-ALKYLATION OF AROMATIC HYDROXYL COMPOUNDS

(75) Inventors: Shawn Marie Dougherty, Gray; Sharon Denise DeBord; Robert Joseph Maleski, both of Kingsport, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/477,857

(22) Filed: Jan. 5, 2000

(51) Int. Cl.$^7$ .................................................. C07C 37/00
(52) U.S. Cl. ........................................... 568/766; 568/788
(58) Field of Search ...................... 568/766, 788

(56) References Cited

U.S. PATENT DOCUMENTS

| | | | |
|---|---|---|---|
| 3,177,259 | * | 4/1965 | Winkle .................................. 568/766 |
| 3,373,210 | | 3/1968 | Nishio et al. . |
| 6,049,015 | * | 4/2000 | Serrano .................................. 568/766 |

FOREIGN PATENT DOCUMENTS

| | | |
|---|---|---|
| 111292 | 6/1964 | (CZ) . |
| 273290 | 1/1992 | (CZ) . |
| 1469896 | 4/1977 | (GB) . |
| 4-103550 | 4/1992 | (JP) . |
| 97/16402 | 5/1997 | (WO) . |

OTHER PUBLICATIONS

J. Pospisil and L. Taimr, Collect. Czech. Chem. Comm., 29 (1964), 381–389.

* cited by examiner

*Primary Examiner*—Michael L. Shippen
(74) *Attorney, Agent, or Firm*—Michael J. Blake; Harry J. Gwinnell

(57) ABSTRACT

Disclosed is a process for the preparation of dialkyl aromatic hydroxyl compounds such as dialkylphenols, dialkylbenzenediols, dialkylnaphthols and dialkylnaphthalenediols, especially 2,5-dialkylhydroquinone, by contacting an aromatic hydroxy compound with an olefin in the presence of a sulfonic acid and sulfuric acid.

10 Claims, No Drawings

PROCESS FOR THE C-ALKYLATION OF AROMATIC HYDROXYL COMPOUNDS

INTRODUCTION

This invention pertains to a novel process for the preparation of dialkyl aromatic hydroxyl compounds such as dialkylphenols, dialkylbenzenediols, dialkylnaphthols and dialkylnaphthalenediols. More specifically, this invention pertains to a process for the preparation of dialkylbenzenediols, especially 2,5-dialkylhydroquinone, by contacting a benzenediol with an olefin in the presence of a sulfonic acid and sulfuric acid.

BACKGROUND OF THE INVENTION

Many processes are known for the preparation of dialkylphenols, dialkylbenzenediols, naphthols and dialkylnaphthalenediols. Czech Patent CS 111,292 describes the alkylation of 2-methylhydroquinone, 2-tert-butylhydroquinone, and 2-tert-octylhydroquinone with diisobutylene in the presence of concentrated sulfuric acid and an inert solvent such as chloroform or a reactive solvent such as acetic acid or excess diisobutylene. The yields reported are of the order of 35%. See also, J. Pospisil and L. Taimr, *Collect. Czech. Chem. Comm.*, 29 (1964), 381–5. British Published Patent Application GB 1,469,896 described a process for the synthesis of a hydroxy-(1,1,3,3-tetramethylbutyl)benzene by the reaction of a hydroxybenzene having one or more hydroxyl groups and optionally substituted, in particular hydroquinone, and a 2,2,4-trimethylpentene, i.e., one of its isomers: α-diisobutylene and β-diisobutylene, or a mixture of the two, in the presence of highly concentrated sulfuric acid and ethylene glycol. According to this patent, highly concentrated sulfuric acid means a concentration in water that is greater than 90%, preferably in the range of 95±3%.

Czech Patent CS 273,290 discloses the preparation of 2,3-bis-(1,1,3,3-tetramethylbutyl)hydroquinone by the alkylation of hydroquinone with diisobutylene using sulfuric acid as a catalyst in a mixture of methanol and aliphatic hydrocarbons. The yield reported is of the order of 65%. U.S. Pat. No. 3,373,210 describes a process wherein the alkylation is carried out in the presence of methanol and sulfuric acid as catalyst to achieve reported yields of 60%. Japanese Kokai 04-103,550 discloses the preparation of dialkylhydroquinones by treating hydroquinone with an olefin containing 6–30 carbon atoms using a strongly acidic polystyrene sulfonic acid-type cation resins wherein the resin preferably consists of particles having a particle diameter of not greater than 0.2 mm. 2,5-Bis(1,1,3,3-tetramethylbutyl)hydroquinone was prepared in a yield of 81% by the reaction of diisobutylene with hydroquinone at 125° C. for 6 hours in the presence of <0.05 mm diameter particles of a strongly acidic polystyrene sulfonic acid resin. Japanese Kokai 04-103,550 also discloses the preparation of 2,5-bis(1,1,3,3-tetramethylbutyl)hydroquinone in a 40% yield by the reaction of diisobutylene with hydroquinone at 35° C. for 6 hours in the presence of acetic, phosphoric and sulfuric acids. Published PCT Patent Document WO 97/16402 discloses a process for the C-alkylation of a hydroxylated aromatic compound having at least one ortho or para hydrogen atom with respect to the hydroxyl group wherein the hydroxylated aromatic compound is contacted with a strong proton acid and a compound which forms a carbocation in the presence of the acid and in the presence of a solvent consisting of a water alcohol couple. In an example, 2,5-di-tert-octylhydroquinone is prepared by contacting hydroquinone with diisobutylene in the presence of water, methanol and benzenesulfonic acid over a period of 8.5 hours to obtain a reaction yield of 74% with an 88% conversion of the hydroquinone.

BRIEF STATEMENT OF THE INVENTION

We have now discovered an improved process for the preparation of dialkyl aromatic hydroxyl compounds such as dialkylphenols, dialkyl-benzenediols, naphthols and dialkylnaphthalenediols. The present invention provides a process for the preparation of dialkyl aromatic hydroxyl compounds such as benzenediols, especially 2,5-dialkylhydroquinone, which comprises contacting an aromatic hydroxyl compounds with an olefin in the presence of a sulfonic acid and sulfuric acid wherein the sulfonic acid:sulfuric acid molar ratio is in the range of about 0.3:1 to 3:1. Our novel process provides dialkyl aromatic hydroxyl compounds in good yields over shorter reaction periods. The product is of high purity, avoiding complex work-up such as alkali washes, thereby increasing product shelf-life. The product precipitates cleanly from the reaction mixture facilitating application in a continuous reactor system. The reaction proceeds readily in a temperature range which minimizes contaminant build-up and avoids the requirement of specialized pressure equipment. Low cost, readily available catalysts are utilized. No organic alcohol or alkane cosolvent is required beyond the reacting olefin itself. The compounds which may be prepared according to the present invention are useful as antioxidants and stabilizers in a variety of products such as oils and fats and petroleum products and as industrial intermediates for the production of surface active agents, coating materials and plastics.

DETAILED DESCRIPTION OF THE INVENTION

The process of our invention comprises contacting an aromatic hydroxyl compound such as a benzenediol with an olefin in the presence of a sulfonic acid and sulfuric acid wherein the sulfonic acid:sulfuric acid molar ratio is in the range of about 0.3:1 to 3:1 to produce a dialkyl aromatic hydroxyl compound such as a dialkylbenzenediol. The process is particularly valuable for the production of 2,5-dialkylhydroquinones from hydroquinone and will be described herein with particular reference to such hydroquinone compounds.

The olefin reactant employed in the process may contain from 3 to 30 carbon atoms, preferably α-olefins containing from 3 to 12 carbon atoms. Examples include, but are in no way are limited to, isobutylene, isoamylene, 1-hexene, 2-methyl-1-pentene, 2-methyl-2-pentene, 1-octene, diisobutylene, 1-decene, 1-dodecene, 2-dodecene, 1-tetradecene, 2-tetradecene, 1-hexadecene, 1-eicosene, α-pinene, camphene, limonene and styrene. Olefin precursors which dehydrate or in some other way eliminate or rearrange under the reaction conditions to form an olefin also may be employed as the olefin source. However, the olefin-generating feedstock should be chosen judiciously to insure that its reactivity or bulk does not slow the conversion, generate contaminants or otherwise affect detrimentally the desired alkylation reaction. Isobutylene and diisobutylene are particular preferred olefin reactants, e.g., for the production of 2,5-bis(tertiary butyl)hydroquinone and 2,5-bis(1,1,3,3-tetramethylbutyl)hydroquinone. The olefin:aromatic hydroxy compound mole ratio normally should be at least 2:1 and typically is in the range of about 3:1 up to 9:1, preferably about 4:1 to 6:1. Since the reaction mixture contains two distinct phases, the reaction of the olefin with the aromatic hydroxy compound is influenced by a variety of factors. Clearly, as in the case of the formation of 2,5-bis(1,1,3,3-tetramethylbutyl)hydroquinone wherein hydroquinone is reacted with two equivalents of olefin, at least two moles of diisobutylene is required for each mole of hydroquinone. Other factors that can minimize excessive olefin requirements include insuring reasonable stir rates and minimizing olefin side reactions.

The alkylation reaction is carried out in the presence of at least one sulfonic acid and sulfuric acid. The sulfonic acid may be selected from a wide variety of halosulfonic acids and aliphatic, cycloaliphatic and aromatic sulfonic acids. Specific examples of the sulfonic acids include fluorosulfonic acid; chlorosulfonic acid; alkane mono- and di-sulfonic acids containing up to about 6 carbon atoms such as methanesulfonic acid, ethanesulfonic acid, ethanedisulfonic acid and trifluoromethanesulfonic acid; aryl mono- and di-sulfonic acids such as benzenesulfonic acid, toluenesulfonic acid, benzenedisulfonic acid, naphthalenesulfonic acid, napthalenedisulfonic acids, camphorsulfonic acid and xylenesulfonic acid. Benzenesulonic acid and the toluenesulfonic acids represent the preferred sulfonic acids. The amount of sulfonic acid employed normally is in the range of about 0.3 to 8 moles of sulfonic acid, preferably about 1 to 4 moles sulfonic acid, per mole of hydroquinone.

The amount of sulfuric acid used may be about 0.1 to 5 moles sulfuric acid, preferably about 0.8 to 4 moles sulfuric acid, per mole of hydroquinone reactant. The mole ratio of the sulfonic acid:sulfuric acid typically is in the range of about 0.3:1 to 3:1, preferably about 0.5 to 2:1, most preferably about 1:1. The process or reaction mixture includes water in a sufficient amount to maintain the sulfonic acid in solution. The use of a substantial excess of water can be detrimental to reaction rate and therefore should be avoided. Although it normally is desirable to minimize the amount of water used, amounts of water slightly greater than that required to maintain the sulfonic acid in solution may be beneficial to separating the phases, e.g., by decantation, of the reaction mixture in product recovery. The water concentration preferably is in the range of about 10 to 20 weight percent, based on the total weight of the process or reaction mixture, i.e., the aromatic hydroxy compound and olefin reactants, the sulfonic and sulfuric acids and the water. An advantage of the present process is that the presence of an alkanol such as methanol is not an essential feature of the process and, therefore, the reaction mixture involved in the process preferably is free essentially free of any alkanol. However, the presence of an alkanol, e.g., an alkanol containing from 1 to about 3 carbon atoms, diol, e.g., a diol containing 2 to 4 carbon atoms, or other water-misicle solvent is not, in general, detrimental to the successful operation of the process. For example, the reaction mixture may contain up to about 75 weight percent of an alkanol, such as methanol, based on the weight of the water present. Although not preferred, the water may be replaced entirely with such an alkanol, diol or other water miscible solvent which is capable of maintaining the sulfonic acid in solution.

The process may be carried out over relatively wide range of temperatures depending, for example, upon the particular reactants employed, the amounts of acids employed, the particular sulfonic acid employed and other process variables. The process most frequently is operated at temperatures in the range of about 35 to 75° C. although solubility problems may occur at lower temperatures and impurity formation and/or slow reaction rates may occur at higher temperatures. The process preferably is carried out at a temperature in the range of about 50 to 70° C., most preferably 55 to 65° C. The process may be carried out under atmospheric (ambient) pressure or elevated pressure.

The process may be operated as a batch process or it may be carried out in a continuous or semi-continuous manner. For example, one mode of continuous operation may comprise continuously feeding in a stream of dissolved aromatic hydroxy compound and a stream of olefin in proportion to the amount of solid product being continuously filtered out. The key is not necessarily to retain an exact level of the sulfonic acid/sulfuric, acid/water mixture, but to keep the ratio of the three components relatively constant. Likewise, in a batch-like process the solid product can be removed and the filtrate can be used directly as the media for conversion of a second batch of olefin and aromatic hydroxy compound. In fact, in as much as the excess olefin from the original reaction does not decompose, dimerize or otherwise change chemical composition, the charge of the olefin in the second reactor can be adjusted accordingly. Likewise unreacted aromatic hydroxy compound or partially reacted variants will manifest themselves as an increase in yield on the recycled reactions. Care must be taken in this manner of batch processing to insure that recycling of the olefin layer is discontinued before build-up of oxidized by-product contaminants, such as quinones of partially- or fully-reacted benzenediols, affects detrimentally product assay, i.e. the purity of the product, since such by-products also are retained. A second batch-like process may involve recycling of the sulfonic acid/sulfuric acid/water phase to the next reaction and recharging only the olefin and aromatic hydroxy compound. The reaction is not dependent as much on the exact amounts of the sulfonic acid, sulfuric acid and water as it is on the relative proportion of these three components. Therefore, the sulfonic acid/sulfuric acid/water phase can be recycled numerous times without adding small quantities of sulfonic acid, sulfuric acid and/or water to compensate for transfer losses. The excess olefin and olefin side-products also can be recycled in a sense in that they can serve as an effective recrystallization solvent.

The process provided by the present invention is further illustrated by the following examples. Unless stated otherwise, the percentages specified in the examples are percent by weight. "Conversion" and "yield" percentages are used synonymously in the examples and are defined as:

$$\frac{\text{Moles 2,5-Bis(1,1,3,3-Tetramethylbutyl)hydroquinone}}{\text{Moles Hydroquinone Fed}} \times 100$$

Conversion levels (area percentages) were determined by the following liquid chromatography test method: A 500 mg sample of the reaction mixture is pipetted from a rapidly stirring reactor and diluted in 50 mL of high-purity acetonitrile. After appropriate instrument/method calibration, the sample is injected into a reverse-phase liquid chromatographic column (Supelco LC-8 15 cm×4.6 mm 5 $\mu$m) using a 0.1M NaOAc buffer/acetonitrile mobile phase with a PE Binary LC pump 250. The concentration of acetonitrile eluent is increased from 70%–100% over 15 minutes. An ultra-violet detector (Applied Biosystems 757 Abs. Detector), set at 280 nm, is used to monitor the component elution. The peak area is recorded relative to the peak area of all the components in the sample.

EXAMPLE 1

To a 500 mL, 4-neck, round-bottom flask equipped with a stirrer, thermocouple and nitrogen are added p-toluenesulfonic acid monohydrate (138.2 g, 0.73 moles), deionized water (25 g), methanol (20 mL), hydroquinone (20 g, 0.18 moles) and diisobutylene (101.8 g, 0.91 moles). This mixture is heated under a nitrogen blanket with stirring to 25–35° C. and then 95% aqueous sulfuric acid (14.0 g, 0.14 moles) is added slowly. The reaction is heated to a reaction temperature of 60° C. After two hours, the conversion of hydroquinone to 2,5-bis(1,1,3,3-tetramethylbutyl) hydroquinone is 34%. After three hours, the conversion of hydroquinone to 2,5-bis(1,1,3,3-tetramethylbutyl) hydroquinone is 38%. Additional 95% aqueous sulfuric acid (3.0 g, 0.03 moles) is added and the reaction is allowed to run overnight. Filtration and recrystallization of the solid results in 70% isolated yield of 2,5-bis(1,1,3,3-tetramethylbutyl)hydroquinone having a purity of 98.8%.

Comparative Example 1

To a 500 ml, 4-neck, round-bottom flask equipped with a stirrer, thermocouple and nitrogen are added p-toluenesulfonic acid monohydrate (138.2 g, 0.73 moles), deionized water (25 g), methanol (20 mL), hydroquinone (20 g, 0.18 moles) and diisobutylene (101.8 g, 0.91 moles). This mixture is heated under a nitrogen blanket with stirring to 58° C. After one hour no mono- or bis(1,1,3,3-tetramethylbutyl)hydroquinone was observed. This example illustrates the results obtained when no sulfuric acid is used.

Comparative Example 2

To a 500 mL, 4-neck, round-bottom flask equipped with a stirrer, thermocouple and nitrogen are added deionized water (25 g), methanol (20 mL), hydroquinone (20 g, 0.18 moles) and diisobutylene (101.8 g, 0.91 moles). This mixture is heated under a nitrogen blanket with stirring to 25–35° C. and then 95% aqueous sulfuric acid (14.0 g, 0.14 moles) is added slowly. The reaction is heated to a reaction temperature of 60° C. After one hour at 60° C., conversion to the desired product, 2,5-bis(1,1,3,3-tetramethylbutyl) hydroquinone is 4.6%. This low level of 2,5-bis(1,1,3,3-tetramethylbutyl)hydroquinone observed within one hour decomposes after two hours and after 5 hours <0.2% of the reaction mixture is 2,5-bis(1,1,3,3-tetramethylbutyl) hydroquinone. This example illustrates the results obtained when no sulfonic acid is used.

EXAMPLE 2

To a 500 ml, 4-neck, round-bottom flask equipped with a stirrer, thermocouple and nitrogen are added 67 weight percent p-toluenesulfonic acid in water (134 g), hydroquinone (20 g, 0.18 moles) and diisobutylene (101.8 g, 0.91 moles). This mixture is heated under a nitrogen blanket with stirring to 25–35° C. and then 95% aqueous sulfuric acid (44.51 g, 0.45 moles) is added slowly. The reaction is heated to a reaction temperature of 60° C. The yield of 2,5-bis(1,1,3,3-tetramethylbutyl)hydroquinone was 58% after 2 hours and 76% after 4.5 hours. The product is isolated after five hours via filtration from the reaction mixture. The solids are recrystallized from 150 mL heptane and isolated to obtain 2,5-bis(1,1,3,3-tetramethylbutyl)hydroquinone having a purity of greater than 98.5% in a 72% yield.

EXAMPLE 3

To a 5000 mL, 3-neck, round-bottom flask equipped with a stirrer, thermocouple and nitrogen are added 67% p-toluenesulfonic acid (PTSA) in water (1340 g), hydroquinone (200 g, 1.8 moles), diisobutylene (1018 g, 9.1 moles) and 95% aqueous sulfuric acid (445.1 g, 4.54 moles). This mixture is heated under a nitrogen blanket with stirring to 58° C. After 14 hours, approximately 88 mole percent of the hydroquinone had been consumed. Diisobutylene (500 g) and water (70 g) were added and the lower aqueous phase (containing PTSA, sulfuric acid, hydroquinone, mono-(1,1, 3,3-tetramethylbutyl)hydroquinone and small amounts of other polar side products) is decanted and transferred into another reactor. The diisobutylene phase is washed with 1500 g water two times at 50° C. and once at 85°. The remaining clear organic phase at 85° C. is cooled to 70° C. and eventually to 0–10° C. and the 2,5-bis(1,1,3,3-tetramethylbutyl)hydroquinone product which crystallizes is collected by filtration. The product is washed with 600 g cold diisobutylene and dried at room temperature overnight. The product was obtained in a yield of 75% and a purity of greater than 98.5%.

EXAMPLE 4

To a 5000 mL, 3-neck, round-bottom flask equipped with a stirrer, thermocouple, nitrogen and the lower phase acid layer from Example 3 at 55° C. are added hydroquinone (200 g, 1.8 moles) and diisobutylene (1018 g, 9.1 moles). This mixture is heated under a nitrogen blanket with stirring to 58° C. After 10–14 hours, approximately 87–94 mole percent ratio of the hydroquinone has been consumed. Diisobutylene (500 g) is added and the lower aqueous phase is transferred to another reactor for further recycles. The diisobutylene phase is washed with 1500 g water two times at 50° C. and once at 85°. The remaining clear organic phase at 85° C. is cooled to 70° C. and eventually to 0–10° C. and the 2,5-bis(1,1,3,3-tetramethylbutyl)hydroquinone product which crystallizes is collected by filtration. The product is washed with 600 g cold diisobutylene and dried at room temperature overnight. The product is obtained in a yield of 86–91%, based on the weight of the hydroquinone reactant, with a purity greater than 98.5%. The PTSA-containing layer can be recycled and used as described in this example until a substantial, e.g., >80%, hinders agitation of the reaction mixture and/or the time and temperature to achieve the desired conversion. Although the formation of significant amounts of by-products such as sulfonated aromatic compounds or their oxidation products has not been observed, formation of such by-products also would limit the extent to which the PTSA-containing layer can be recycled advantageously.

EXAMPLE 5

To a 500 mL, 3-neck, round-bottom flask equipped with a stirrer, thermocouple and nitrogen are added 67 weight percent p-toluenesulfonic acid (PTSA) in water (33.5 g), hydroquinone (20.0 g, 0.18 moles), diisobutylene (101.8 g, 0.91 moles) and 95% aqueous sulfuric acid (11.2 g, 0.112 moles). This mixture is heated to 58° C. under a nitrogen blanket with stirring. After 14 hours reaction time at 58° C., diisobutylene (50 g) is added and the lower aqueous phase (containing PTSA, sulfuric acid, hydroquinone, mono-(1,1, 3,3-tetramethylbutyl)hydroquinone and small amounts of other polar side products) is transferred to another reactor. The diisobutylene phase is washed with 150 g water two times at 50° C. and once at 85°. The remaining clear organic phase at 85° C. is cooled to 70° C. and eventually to 0–10° C. and the 2,5-bis(1,1,3,3-tetramethylbutyl)hydroquinone product which crystallizes is collected by filtration. The product is washed with 60 g cold diisobutylene and dried at room temperature overnight. The 2,5-bis(1,1,3,3- tetramethylbutyl)hydroquinone product is obtained in a yield of 73% product and a purity greater than 98.5%.

The invention has been described in detail with particular reference to preferred embodiments thereof, but it will be understood that variations and modifications can be effected within the spirit and scope of the invention.

We claim:

1. Process for the preparation of dialkyl aromatic hydroxyl compounds which comprises contacting an aromatic hydroxyl compound with an olefin in the presence of a sulfonic acid and sulfuric acid wherein the sulfonic acid:sulfuric acid molar ratio is in the range of about 0.3:1 to 3:1.

2. Process according to claim 1 wherein the dialkyl aromatic hydroxyl compound is a dialkylphenol, dialkylbenzenediol, naphthol or a dialkylnaphthalenediols, the aromatic hydroxyl compound is phenol, a benzenediol, a napthol or a naphthalenediol, and the olefin is an α-olefins containing from 3 to 12 carbon atoms.

3. Process for the preparation of a 2,5-dialkylhydroquinone which comprises contacting hydroquinone with an olefin containing from 3 to 12 carbon atoms in the presence of a sulfonic acid and sulfuric acid wherein the sulfonic acid:sulfuric acid molar ratio is in the range of about 0.3:1 to 3:1 wherein the amount of sulfuric acid used is about 0.1 to 5 moles sulfuric acid per mole of hydroquinone reactant, the amount of sulfonic acid employed is about 0.3 to 8 moles of sulfonic acid per mole of hydroquinone, the process reaction mixture contains water in an amount which is sufficient to maintain the sulfonic acid in solution, and the process is carried out at a temperature of about 35 to 75°.

4. Process according to claim 3 wherein the amount of sulfuric acid used is about 0.8 to 4 moles sulfuric acid per mole of hydroquinone reactant, the sulfonic acid is benzenesulfonic acid or toluenesulfonic acid, the amount of sulfonic acid employed is about 1 to 4 moles of sulfonic acid per mole of hydroquinone, the process reaction mixture contains about 10 to 20 weight percent water based on the total weight of the process reaction mixture, and the process is carried out at a temperature of about 55 to 65°.

5. Process for the preparation of 2,5-bis(1,1,3,3-tetramethylbutyl)hydroquinone which comprises contacting hydroquinone with diisobutylene in the presence of a sulfonic acid and sulfuric acid wherein the sulfonic acid:sulfuric acid molar ratio is in the range of about 0.5:1 to 2:1.

6. Process according to claim 5 wherein the amount of sulfuric acid used is about 0.2 to 5 moles sulfuric acid per mole of hydroquinone reactant, the amount of sulfonic acid employed is about 0.3 to 8 moles of sulfonic acid per mole of hydroquinone, the process reaction mixture contains water in an amount which is sufficient to maintain the sulfonic acid in solution, and the process is carried out at a temperature of about 50 to 70°.

7. Process according to claim 5 wherein the amount of sulfuric acid used is about 0.8 to 4 moles sulfuric acid per mole of hydroquinone reactant, the sulfonic acid is benzenesulfonic acid or toluenesulfonic acid, the amount of sulfonic acid employed is about 1 to 4 moles of sulfonic acid per mole of hydroquinone, the process reaction mixture contains about 10 to 20 weight percent water based on the total weight of the process reaction mixture, and the process is carried out at a temperature of about 55 to 65°.

8. Process for the preparation of 2,5-bis(tertiary butyl) hydroquinone which comprises contacting hydroquinone with isobutylene in the presence of a sulfonic acid and sulfuric acid wherein the sulfonic acid:sulfuric acid molar ratio is in the range of about 0.5:1 to 2:1.

9. Process according to claim 8 wherein the amount of sulfuric acid used is about 0.2 to 5 moles sulfuric acid per mole of hydroquinone reactant, the amount of sulfonic acid employed is about 0.3 to 8 moles of sulfonic acid per mole of hydroquinone, the process reaction mixture contains water in an amount which is sufficient to maintain the sulfonic acid in solution, and the process is carried out at a temperature of about 35 to 75°.

10. Process according to claim 8 wherein the amount of sulfuric acid used is about 0.8 to 4 moles sulfuric acid per mole of hydroquinone reactant, the sulfonic acid is benzenesulfonic acid or toluenesulfonic acid, the amount of sulfonic acid employed is about 1 to 4 moles of sulfonic acid per mole of hydroquinone, the process reaction mixture contains about 10 to 20 weight percent water based on the total weight of the process reaction mixture, and the process is carried out at a temperature of about 50 to 70°.

* * * * *